(12) United States Patent
Brodsky et al.

(10) Patent No.: US 8,673,321 B2
(45) Date of Patent: Mar. 18, 2014

(54) CYCLOPHOSPHAMIDE IN COMBINATION WITH ANTI-IDIOTYPIC VACCINES

(75) Inventors: Robert A. Brodsky, Brooklandville, MD (US); Richard J. Jones, Baltimore, MD (US); Francis E. O'Donnell, Jr., Town and Country, MO (US); Susan Bonitz, Flemington, NJ (US); Carlos Santos, Tampa, FL (US)

(73) Assignees: The Johns Hopkins University, Baltimore, MD (US); Accentia Biopharmaceuticals, Inc., Tampa, FL (US)

( * ) Notice: Subject to any disclaimer, the term of this patent is extended or adjusted under 35 U.S.C. 154(b) by 0 days.

(21) Appl. No.: 13/230,212

(22) Filed: Sep. 12, 2011

(65) Prior Publication Data

US 2012/0148611 A1 Jun. 14, 2012

Related U.S. Application Data

(63) Continuation of application No. 13/017,817, filed on Jan. 31, 2011, now abandoned, which is a continuation of application No. 12/818,380, filed on Jun. 18, 2010, now abandoned, which is a continuation of application No. 12/610,798, filed on Nov. 2, 2009, now abandoned, which is a continuation of application No. 12/404,891, filed on Mar. 16, 2009, now abandoned, which is a continuation of application No. PCT/US2007/078521, filed on Sep. 14, 2007.

(60) Provisional application No. 60/844,830, filed on Sep. 15, 2006.

(51) Int. Cl.
A61K 45/00 (2006.01)
A61K 39/395 (2006.01)
A61K 31/675 (2006.01)

(52) U.S. Cl.
USPC .................. 424/278.1; 424/144.1; 514/90

(58) Field of Classification Search
None
See application file for complete search history.

(56) References Cited

U.S. PATENT DOCUMENTS

| | | |
|---|---|---|
| 4,537,883 A | 8/1985 | Alexander et al. |
| 4,753,965 A | 6/1988 | Stemerick et al. |
| 4,841,085 A | 6/1989 | Farquhar et al. |
| 5,036,060 A | 7/1991 | Alam et al. |
| 5,055,459 A | 10/1991 | Andersson et al. |
| 5,187,266 A | 2/1993 | Farquhar et al. |
| 5,204,369 A | 4/1993 | Vallee et al. |
| 5,413,995 A | 5/1995 | Alexander et al. |
| 5,624,910 A | 4/1997 | Vallee et al. |
| 5,649,904 A | 7/1997 | Gianni |
| 5,866,169 A | 2/1999 | Hausheer et al. |
| 5,876,956 A | 3/1999 | Jones et al. |
| 5,886,028 A | 3/1999 | Vallee et al. |
| 5,914,257 A | 6/1999 | Fukaya et al. |
| 6,121,010 A | 9/2000 | Vallee et al. |
| 6,255,497 B1 | 7/2001 | Vallee et al. |
| 6,268,138 B1 | 7/2001 | Dalla-Favera et al. |
| 6,288,110 B1 | 9/2001 | Marikovsky |
| 6,428,782 B1 | 8/2002 | Slavin et al. |
| 6,447,767 B1 | 9/2002 | Slavin et al. |
| 6,465,436 B2 | 10/2002 | Lukas et al. |
| 6,544,787 B1 | 4/2003 | Slavin et al. |
| 6,558,662 B2 | 5/2003 | Sykes et al. |
| 6,562,347 B1 * | 5/2003 | Kwak et al. ................. 424/192.1 |
| 6,627,759 B1 | 9/2003 | Smith et al. |
| 6,936,599 B2 | 8/2005 | Voskuhl |
| 7,368,434 B2 | 5/2008 | Keung et al. |
| 7,408,039 B2 | 8/2008 | Sykes et al. |
| 7,531,562 B2 | 5/2009 | Fahl et al. |
| 7,754,480 B2 | 7/2010 | Smith et al. |
| 7,892,578 B2 | 2/2011 | Sykes et al. |
| 2001/0053362 A1 | 12/2001 | Walters |
| 2002/0048584 A1 | 4/2002 | Pomerantz |
| 2003/0007968 A1 | 1/2003 | Larsen et al. |
| 2003/0073649 A1 | 4/2003 | DiMartino et al. |
| 2003/0099622 A1 | 5/2003 | Hering et al. |
| 2004/0023318 A1 | 2/2004 | Smith et al. |
| 2004/0064037 A1 | 4/2004 | Smith |
| 2004/0152630 A1 | 8/2004 | Fu et al. |
| 2004/0214902 A1 | 10/2004 | Wang et al. |
| 2005/0108067 A1 | 5/2005 | Chapman et al. |
| 2005/0201980 A1 | 9/2005 | Moran |
| 2005/0272698 A1 | 12/2005 | Daftary et al. |
| 2006/0002930 A1 | 1/2006 | Brunetta et al. |
| 2006/0229233 A1 | 10/2006 | Frenkel et al. |

(Continued)

FOREIGN PATENT DOCUMENTS

WO WO-96/36344 11/1996
WO WO-98/20932 A2 5/1998

(Continued)

OTHER PUBLICATIONS

Davis et al (Biology of Blood and Bone Marrow Transplantation, 2001, vol. 7, pp. 517-522).*

(Continued)

*Primary Examiner* — Karen Canella
(74) *Attorney, Agent, or Firm* — Foley Hoag LLP

(57) ABSTRACT

The present invention relates to methods of treating a cancer and in particular, a B-cell derived cancer, using a lymphocytotoxic but hematopoeitic cell sparing high-dose pulsed amount of an oxazaphosphorine drug in combination with immune therapeutics such as, for example, an autologous idiotypic vaccine and monoclonal antibodies that selectively bind B-cell specific antigens.

26 Claims, No Drawings

(56) References Cited

U.S. PATENT DOCUMENTS

| | | | |
|---|---|---|---|
| 2006/0253263 | A1 | 11/2006 | Meshkin |
| 2007/0173442 | A1 | 7/2007 | Vollmer |
| 2007/0202077 | A1 | 8/2007 | Brodsky et al. |
| 2011/0082115 | A1 | 4/2011 | O'Donnell, Jr. et al. |
| 2011/0092462 | A1 | 4/2011 | Brodsky et al. |
| 2011/0097426 | A1 | 4/2011 | O'Donnell, Jr. et al. |
| 2011/0117050 | A1 | 5/2011 | O'Donnell, Jr. et al. |

FOREIGN PATENT DOCUMENTS

| | | |
|---|---|---|
| WO | WO-98/42378 | 10/1998 |
| WO | WO-99/42099 | 8/1999 |
| WO | WO-00/27428 | 5/2000 |
| WO | WO-00/40701 A2 | 7/2000 |
| WO | WO-00/74718 | 12/2000 |
| WO | WO-2005/057213 A1 | 6/2005 |
| WO | WO-2007/065167 | 6/2007 |
| WO | WO-2008/034071 | 3/2008 |
| WO | WO-2008/034074 | 3/2008 |
| WO | WO-2008/034076 | 3/2008 |
| WO | WO-2008/156494 A1 | 12/2008 |
| WO | WO-2009/045464 | 4/2009 |
| WO | WO-2009/067690 A2 | 5/2009 |
| WO | WO-2009/067699 A2 | 5/2009 |
| WO | WO-2009/094456 | 7/2009 |

OTHER PUBLICATIONS

Pallera et al, (The Journal of Supportive Oncology, vol. 2, pp. 223-247).*
Petri et al (Arthritis and Rheumatism, 2003, vol. 48, pp. 166-173).*
Pallera et al, (The Journal of Supportive Oncology, 2004 vol. 2, pp. 223-247).
Chung, D. et al., "Anti-Thymocyte Globulin Prevents Autoimmune Encephalomyelitis by Expanding Myelin Antigen Specific Foxp3+ Regulatory T Cell," Clinical Immunology, 123:S10-S11 (2007) Abstract.
Maksymowych et al., "Evaluation and Validation of the Patient Acceptable Symptom State (PASS) in Patients With Ankylosing Spondylitis," Arthritis & Rheumatism, 57(1):133-139 (2007).
Mickey, M.R. et al., "Correlation of Clinical and Immunologic States in Multiple Sclerosis," Arch Neurol, 44:371-375 (1987).
Moody, D.J. et al., "Administration of Monthly-Pulse Cyclophosphamide in Multiple Sclerosis Patients. Effects of Long-Term Treatment on Innunologic Parameters," J. Neuroimmunology, 14:161-173 (1987).
Moreb et al., "Heterogeneity of Aldehyde Dehydrogenase Expression in Lung Cancer Cell Lines is Revealed by Aldefluor Flow Cytometry-Based Assay," Cytometry Part B (Clin Cyto), 72B:281-289 (2007).
Uitdehaag, B.M.J. et al., "Long-Lasting Effects of Cyclophosphamide on Lymphocytes in Peripheral Blood and Spinal Fluid," Acta Neurol. Scand., 79:12-17 (1989).
European Search Report dated Oct. 17, 2011 from EP 08836174.6.
International Search Report dated Dec. 16, 2008, from PCT/US08/11402.
Adamkiewicz, T.V. et al. "Unrelated cord blood transplantation in children with sickle cell disease: Review of four-center experience" *Pediatr Transplantation*, 2007, 11:641-644.
Alyea, E.P. et al. "Comparative outcome of nonmyeloablative and myeloablative allogeneic hematopoietic cell transplantation for patients older than 50 years of age" *Blood*, Feb. 15, 2005, 105(4):1810-1814.
Alyea, E.P. et al. "Impact of Conditioning Regimen Intensity on Outcome of Allogeneic Hematopoietic Cell Transplantation for Advanced Acute Myelogenous Leukemia and Myelodysplastic Syndrome" *Biology of Blood and Marrow Transplantation*, 2006, 12:1047-1055.
Anderson, L.W. et al. "Cyclophosphamide and 4-Hydroxycyclophosphamide/Aldophosphamide Kinetics in Patients Receiving High-Dose Cyclophosphamide Chemotherapy" *Clinical Cancer Research*, Sep. 1996, 2:1481-1487.
Attema-De Jonge, M.E. "Pharmacokinetically guided dosing of (high-dose) chemotherapeutic agents" Thesis University Utrecht, Dec. 17, 2004, pp. 1-313.
Awad, a. et al., "Cyclophosphamide in Multiple Sclerosis: Scientific Rationale, History and Novel Treatment Paradigms," Ther Adv Neurol Disord, 2(6):357-368 (2009).
Bacigalupo, a. et al. "Defining the Intensity of Conditioning Regimens: working definitions" *Biol Blood Marrow Transplant*, Dec. 2009, 15(12):1628-1633.
Baron, F. et al. "Allogeneic Hematopoietic Cell Transplantation Following Nonmyeloablative Conditioning as Treatment for Hematologic Malignancies and Inherited Blood Disorders" *Molecular Therapy*, Jan. 2006, 13(1):26-41.
Bernaudin, F. et al. "Long-term results of related myeloablative stem-cell transplantation to cure sickle cell disease" *Blood*, Oct. 1, 2007, 110(7):2749-2756.
"Biovest Secures Worldwide Exclusive License to Late-Stage Technology for Elimination of Transplant Rejection" Press Release, Jan. 22, 2008 at 08:30 AM EST.
Brannagan, T.H., 3rd, Alaedini, A., Gladstone, D.E. "High-dose cyclophosphamide without stem cell rescue for refractory multifocal motor neuropathy," Muscle Nerve, Aug;34(2):246-50 (2006).
Brannagan, T.H. et al., "High-dose Cyclophosphamide Without Stem-cell Rescue for Refractory CIDP," Neurology, 58:1856-1858 (2002).
Brien, J.F. et al. "Aldehyde dehydrogenase inhibitors as alcohol-sensitizing drugs: a pharmacological perspective" *TIPS*, Dec. 1985, 477-480.
Brodsky, R.A., "Acquired Severe Aplastic Anemia in Children: Is there a standard of care?" Pediatric Blood and Cancer, 43(7):711-2 (2004).
Brodsky, R.A., "Biology and management of acquired severe aplastic anemia," Current Opinion in Oncology, 10:95-99 (1998) (abstract only).
Brodsky, R.A., Smith, B.D., "Bone marrow transplantation for autoimmune diseases," Current Opinion in Oncology, 11: 83-86 (1999).
Brodsky, R.A., "High dose cyclophosphamide treatment for autoimmune disorders," The Scientific World Journal 2:1808-1815 (2002).
Brodsky, R.A., "High-dose cyclophosphamide for aplastic anemia and autoimmunity," Current Opinion in Oncology, 14:143-146 (2002).
Brodsky, R.A. et al. "Multicenter phase 3 study of the complement inhibitor eculizumab for the treatment of patients with paroxysmal nocturnal hemoglobinuria" Blood, Feb. 15, 2008, 111(4):1840-1847.
Brodsky, R.A. "Reduced intensity HLA-haploidentical BMT with post transplantation cyclophosphamide in nonmalignant hematologic diseases" *Bone Marrow Transplant*, Oct. 2008, 42(8):523-527.
Brodsky, R.A., Jones, R.J., "Riddle: What do aplastic anemia, acute promyelocytic leukemia, and chronic myeloid leukemia have in common?" Leukemia, 18(10):1740-2 (2004).
Brodsky, Robert, A., et al.; "Complete Remission in Severe Aplastic Anemia After High-Dose Cyclophosphamide Without Bone Marrow Transplantation", Blood, vol. 87, No. 2, Jan. 15, 1996, pp. 491-494.
Brodsky, Robert A., et al.; "Durable Treatment-Free Remission after High-Dose Cyclophosphamide Therapy for Previously Untreated Severe Aplastic Anemia", Annals of Internal Medicine, vol. 135 No. 7, Oct. 2, 2001, pp. 477-483.
Brodsky, Robert A., et al.; "Elimination of alloantibodies by immunoablative high-dose cyclophosphamide" Transplantation (Baltimore), vol. 71, No. 3, pp. 482-484 (Feb. 15, 2001).
Brodsky, Robert A., et al.; "High-dose cyclophosphamide as salvage therapy for severe aplastic anemia," Experimental Hematology (New York), vol. 32, No. 5, May 2004; pp. 435-440, XP002430102 (ISSN: 0301-472X).
Brodsky, Robert, A., et al.; "Immunoablative High-Dose Cyclophosphamide without stem-Cell Rescue for Refractory, Severe Autoimmune Disease", Annals of Internal Medicine, vol. 129, Issue 12, Dec. 15, 1998, pp. 1031-1035.
Brown, R.A. et al. "High-Dose Etoposide, Cyclophosphamide, and Total Body Irradiation With Allogeneic Bone Marrow Transplanta-

(56) References Cited

OTHER PUBLICATIONS tion for Patients With Acute Myeloid Leukemia in Untreated First Relapse: A Study by the North American Marrow Transplant Group" *Blood,* Mar. 1, 1995, 85(5):1391-1395.

Burroughs, L. et al. "Comparison of Allogeneic Hematopoietic Cell Transplantation (HCT) after Nonmyeloablative Conditioning with HLA-Matched Related (MRD), Unrelated (URD), and Related Haploidentical (Haplo) Donors for Relapsed or Refractory Hodgkin Lymphoma (HL)" *Blood (ASH Annual Meeting Abstracts),* 2007, 110: Abstract 173.

Burroughs, L.M. et al. "Comparison of Outcomes of HLA-Matched Related, Unrelated, or Hla-Haploidentical Related Hematopoietic Cell Transplantation following Nonmyeloablative Conditioning for Relapsed or Refractory Hodgkin Lymphoma" *Biol Blood Marrow Transplant,* Nov. 2008, 14(11):1279-1287.

Cohen, L. "Optimization of Dose-Time Factors for a Tumor and Multiple Associated Normal Tissues" Int. J. Radiation Oncology Biol. Phys., Feb. 1987, 13(2):251-258.

D'Cruz, D. et al., "High-dose Intravenous Cyclophosphamide Therapy in Severe SLE," Lupus, 11:403-404 (2002).

DeAngelis, T. et al., "Multiple Sclerosis: New Treatment Trials and Emerging Therapeutic Targets," Neurology, 21:261-271 (2008).

de Bittencourt, P.R.M. et al., "Mutliple sclerosis: long-term remission after a high dose of cyclophosphamide," Acta Neurol Scan, 111:195-198 (2005).

Demirer, T. et al. "High-Dose Cyclophosphamide, Carmustine, and Etoposide Followed by Allogeneic Bone Marrow Transplantation in Patients With Lymphoid Malignancies Who Had Received Prior Dose-Limiting Radiation Therapy" *J Clin Oncol,* Mar. 1995, 13(3):596-602.

Dezern, A.E. et al. "Post-transplantation cyclophosphamide for GVHD prophylaxis in severe aplastic anemia" *Bone Marrow Transplantation,* 2010, pp. 1-2.

Djulbegovic, B. et al. "Nonmyeloablative Allogeneic Stem-Cell Transplantation for Hematologic Malignancies: A Systematic Review" *Cancer Control,* 2003, 10(1):17-41.

Dockham, P.A. et al. "Relative Contribution of Human Erythrocyte Aldehyde Dehydrogenase to the Systemic Detoxification of the Oxazaphosphorines" Drug Metabolism and Disposition, 1997, 25(12):1436-1441.

Drachman, Daniel B., et al.; "High-dose therapy for autoimmune neurologic diseases," Current Opinion in Oncology; vol. No. 2, Mar. 2005; pp. 83-88, XP009082245 (ISSN: 1040-8746).

Drachman, Daniel B., et al.; "Treatment of refractory myasthenia: "Rebooting" with high-dose cyclophosmphamide," Annals of Neurology, vol. 53, No. 1, Jan. 2003, pp. 29-34, XP009082013 (ISSN: 0364-5134 Abstract).

Droz, J.P. et al. "Failure of High-Dose Cyclophosphamide and Etoposide Combined with Double-Dose Cisplatin and Bone Marrow Support in Patients with High-vol. Metastatic Nonseminomatous Germ-Cell Tumours: Mature Results of a Randomised Trial" *European Urology,* 2007, 51:739-748.

Emadi, A. et al. "Cyclophosphamide and cancer: golden anniversary" Nat. Rev. Clin. Oncol., Nov. 2009, 6:638-647.

Eto, M. et al. "Specific Destruction of Host-Reactive Mature T Cells of Donor Origin Prevents Graft-Versus-Host Disease in Cyclophosphamide-Induced Tolerant Mice" *The Journal of Immunology,* Mar. 1, 1991, 146(5):1402-1409.

Freeman E., "High Time for HiCy," Hopkins Medicine, pp. 21-26, Winter 2008.

Fuchs et al., "Post-transplantation cyclophosphamide (Cy) reduces graft rejection and graft-versus-host disease (GVHD) after non-myeloblative, partially HLA-mismatched (haploidentical) bone marrow transplantation (BMT)," Blood, 104(11):128A, Abstract.

Gauthier, S.A. et al., "Cyclophosphamide Therapy for MS," The International MS Journal, 12:52-58 (2005).

Germolec, D.R. et al. "Induction of CYP1A1 and Aldh-3 in Lymphoid Tissues from Fisher 344 Rats Exposed to 2,3,7,8-Tetrachlorodibenzodioxin (TCDD)" Toxicology and Applied Pharmacology, 1996, 137:57-66.

Ginestier, C. et al. "ALDH1 is a marker of normal and malignant human mammary stem cells and a predictor of poor clinical outcome" Cell Stem Cell, Nov. 15, 2007, 1(5):555-567.

Gladstone, D.E., et al., "High-Dose Cyclophosphamide for Moderate to Severe Refractory Multiple Sclerosis," Arch Neurol., 63:1388-1393 (2006).

Gladstone, D.E., et al., "High-dose Cyclophosphamide for Severe Systemic Lupus Erythematosus," Lupus, 11(7):405-410 (2002).

Gladstone, D.E. and Brannagan, T.H., "High dose cyclophosphamide for severe refractory myasthenia gravis," Journal of Neurology, Neurosurgery and Psychiatry, 75:789-791 (2004).

Gladstone, D.E., Prestrud, A.A., Brannagan, T.H., 3rd., "High-dose cyclophosphamide results in long-term disease remission with restoration of a normal quality of life in patients with severe refractory chronic inflammatory demyelinating polyneuropathy," J Peripher Nery Syst., Mar;10(1):11-6 (2005).

Groot et al. "Aldehyde Dehydrogenase Inveolvement in a variant of the Brown Norway Rat Acute Myelocytic Leukaemia (BNML) that acquired cyclophosphamide resistance in vivo" European Journal of Cancer, vol. 30A, No. 14, pp. 2137-2143, 1994.

Hacker, M.P. et al. "Effect of Disulfiram (Tetraethylthiuram Disulfide) and Diethyldithiocarbamate on the Bladder Toxicity and Antitumor Activity of Cyclophosphamide in Mice" Cancer Research, Nov. 1982, 42:4490-4494.

Hadidi, A.H.F.A. et al. "Phenotypically Deficient Urinary Elimination of Carboxyphosphamide after Cyclophosphamide Administration to Cancer Patients". Cancer Research, Sep. 15, 1988, 48:5167-5171.

Hansell, N. K. et al. "Erythrocyte Aldehyde Dehydrogenase Activity: Lack of Association with Alcohol Use and Dependence or Alcohol Reactions in Australian Twins" Alcohol & Alcoholism, 2005, 40(5):343-348.

Helander, A. "Aldehyde Dehydrogenase in Blood: Distribution, Characteristics and Possible Use as Marker of Alcohol Misuse" Alcohol & Alcoholism, 1993, 28(2):135-145.

Helander, A. et al. "Comparision of Blood Aldehyde Dehydrogenase Activities in Moist Snuff Users, Cigarette Smokers and Nontobacco Users" Alcohol Clin Exp Res, 1991, 15(1):1-6.

Henze, T. "Managing Specific Symptoms in People with Multiple Sclerosis" The International MS Journal, 2005, 12:60-68.

Hess, D.A. et al. "Selection based on CD133 and high aldehyde dehydrogenase activity isolates long-term reconstituting human hematopoietic stem cells" *Blood,* Mar. 1, 2006, 107(5):2162-2169.

Hillmen, P. et al. "The Complement Inhibitor Eculizumab in Paroxysmal Nocturnal Hemoglobinuria" *N Engl J Med,* Sep. 21, 2006, 355(12):1233-1243.

Hilton, J. "Role of Aldehyde Dehydrogenase in Cyclophosphamide-resistant L1210 Leukemia" Cancer Res, Nov. 1, 1984, 44:5156-5160.

Horan, J.T. et al. "Hematopoietic stem cell transplantation for multiply transfused patients with sickle cell disease and thalassemia after low-dose total body irradiation, fludarabine, and rabbit anti-thymocyte globulin" *Bone Marrow Transplantation,* 2005, 35:171-177.

Hsu, Frank J., et al. "Vaccination of patients with B-cell lymphoma using autologous antigen-pulsed dendritic cells," Nature Medicine, 2(1):52-58 (Jan. 1996).

Huhn, Richard D., et al.; High-dose Cyclophosphamide with Autologous Lymphocyte-depleted Peripheral Blood Stem Cell (PFSC) Support for Treatment of Refractory Chronic Autoimmune Thrombocytopenia, BLOOD, vol. 101, No. 1, Jan. 1, 2003, pp. 71-77.

Huzly, D. et al. "Routine Immunizations in Adult Renal Transplant Recipients." *Transplantation,* 63:839-845. Published Mar. 1997.

Iannone, R. et al. "Results of Minimally Toxic Nonmyeloablative Transplantation in Patients with Sickle Cell Anemia and βThalassemia" *Biology of Blood and Marrow Transplantation,* 2003, 9:519-528.

Jalla, S. et al. "Cyclophosphamide Plus Allogeneic CD4+ T Cell Infusion Induces Anti-Lymphoma Immunity Despite Lack of Graft-Versus-Host Disease (GVHD) or Sustained Engraftment" *Blood (ASH Annual Meeting abstracts),* 2004, 104: Abstract 3063.

Jeavons, C.M. et al. "Effects of Elevated Female Sex Steroids on Ethanol and Acetaldehyde Metabolism in Humans" Alcohol Clin Exp Res, 1984, 8(4):352-358.

(56) References Cited

OTHER PUBLICATIONS

Jones, R.J. et al. "Assessment of Aldehyde Dehydrogenase in Viable Cells" Blood, May 15, 1995, 85(10):2742-2746.

Kasamon, Y.L. et al. "Greater HLA Disparity Is Associated with Reduced Risk of Relapse and Improved Event-Free Survival after Nonmyeloablative, HLA-Haploidentical BMT with Post-Transplantation High-Dose Cyclophosphamide" Blood (ASH Annual Meeting abstracts), 2008, 112: Abstract 150.

Kasamon, Y.L. et al. "Immunologic recovery following autologous stem-cell transplantation with pre-and posttransplantation rituximab for low-grade or mantle cell lymphoma" Annals of Oncology, Jun. 2010, 21(6):1203-1210.

Kasamon, Y.L. et al. "Nonmyeloablative HLA-Haploidentical BMT with High-Dose Posttransplantation Cyclophosphamide: Effect of HLA Disparity on Outcome" Biol Blood Marrow Transplant, Apr. 2010, 16(4):482-489.

Kastan, M.B. et al. "Direct Demonstration of Elevated Aldehyde Dehydrogenase in Human Hematopoietic Progenitor Cells" Blood, May 15, 1990, 75(10):1947-1950.

Kerr D. et al., "Revimmune: Delivering a knockout punch to autoimmune diseases," Specialty Pharma—Therapeutic Focus, 7, vol. 7, No. 6, pp. 80-83 (Jun. 2007).

Kohn, F.R. et al. "Aldehyde Dehydrogenase Activity as the Basis for the Relative Insensitivity of Murine Pluripotent Hematopoietic Stem Cells to Oxazaphosphorines" Biochemical Pharmacology, 1985, 34(19):3465-3471.

Kohn, F.R. et al. "Effect of Aldehyde Dehydrogenase Inhibitors on the ex Vivo Sensitivity of Human Multipotent and Committed Hematopoietic Progenitor Cells and Malignant Blood Cells to Oxazaphosphorines" Cancer Research, Jun. 15, 1987, 47:3180-3185.

Kohn, F.R. et al. "Effect of Aldehyde Dehydrogenase Inhibitors on the ex Vivo Sensitivity of Murine Late Spleen Colony-Forming Cells (Day-12 CFU-S) and Hematopoietic Repopulating Cells to Mafosfamide (Asta Z 7557)" Biochemical Pharmacology, 1987, 36(17):2805-2811.

Krishnan, C. et al., "Reduction of Disease Activity and Disability with High-Dose Cyclophosphamide in Patients With Aggressive Multiple Sclerosis," Arch Neurol., 65(8):1044-1051 (2008).

Krishnan, C. et al., "Reduction of Disease Activity and Disability With High-Dose Cyclophosphamide in Patients With Aggressive Multiple Sclerosis," Arch Neurol, 65(8):E1-E8 (2008).

Krishnan, Drachman, et al. "High-Dose Cyclophosphamide in the Treatment of Aggressive Multiple Sclerosis," (American Academy of Neurology (AAN) Annual Meeting: 2006 Abstract (Apr. 4, 2006).

Kumar, P. et al. "Chemoprotective action of Septilin against Cyclophosphamide Toxicity" Indian Journal of Pharmaceutical Sciences, 1995, 57(5):215-217.

Kwak, L.W. et al. "Vaccination with syngeneic, lymphoma-derived immunoglobulin idiotype combined with granulocyte/macrophage colony-stimulating factor primes mice for a protective T-cell response" Proc. Natl. Acad. Sci. USA, Oct. 1996, 93:10972-10977.

La Mantia, L. et al., "Cyclophosphamide for multiple sclerosis (Review)," Cochrane Database of Systematic Reviews 2002, 3:1-22.

La Mantia, L. et al., "Cyclophosphamide for multiple sclerosis (Review)," Cochrane Database of Systematic Reviews 2007, 1:1-23.

Levy, M.Y. et al. "Clinical Tumor Responses Despite Graft Rejection after Nonmyeloablative Conditioning and Transplantation of Partially HLA-Mismatched (Haploidentical) Bone Marrow" Blood (ASH Annual Meeting Abstracts), 2005, 106: Abstract 2897.

Lin, K.H. et al. "Regulation of Aldehyde Dehydrogenase Activity in Five Rat Hepatoma Cell Lines" Cancer Res, Nov. 1984, 44:5219-5226.

Lin, P.T., Martin, B.A., Weinacker, A.B., So, Y.T., "High-dose cyclophosphamide in refractory myasthenia gravis with MuSK antibodies," Muscle Nerve, Mar.; 33:433-5 (2006).

Lindahl, R. "Aldehyde Dehydrogenases and Their Role in Carcinogensis" Critical Reviews in Biochemistry and Molecular Biology, 1992, 27(4,5):283-335.

Lioznov, M.V. et al. "Aldehyde dehydrogenase activity as a marker for the quality of hematopoietic stem cell transplants" Bone Marrow Transplantation, 2005, 35:909-914.

Ljungman, P. et al. "Special Report: Vaccination of stem cell transplant recipients: recommendations of the Infectious Diseases Working Party of the EBMT" Bone Marrow Transplantation, 2005, 35:737-746.

Luznik et al., "Durable engraftment of major histocompatibility complex-incompatible cells after nonmyeloablative conditioning with fludarabine, low-dose total body irradiation, and post-transplantation cyclophosphamide," Blood, 98:3456-3464 (2001).

Luznik, et al., "Post-Transplantation High-Dose Cyclophosphamide (Cy) Is Effective Single Agent GVHD Prophylaxis That Permits Prompt Immune Reconstitution after Myeloablative HLA Matched Related and Unrelated Bone Marrow Transplantation (BMT)," Session Type: Poster Session, Board #120-III, presented at American Society of Hematology (ASH) Annual Meeting Dec. 11, 2006; Abstract #2891 appears in Blood, vol. 108, issue 11, (Nov. 16, 2006).

Luznik, et al., "Post-Transplantation high-dose cyclophosphamide (Cy) is an effective single agent GVHD prophylaxis that permits prompt immune reconstitution after myeloablative HLA matched related and unrelated bone marrow transplantation (BMT)," Biology of Blood and Marrow Transplantation, vol. 13, Issue 2, Supplement 1, (Feb. 2007), p. 4, Abstracts from the 2007 BMT Tandem Meetings; Available online Jan. 25, 2007.

Luznik, L. et al. "High-dose cyclophosphamide as single-agent, short-course prophylaxis of graft-versus-host disease" Blood, Apr. 22, 2010, 115(16):3224-3230.

Luznik, L. et al. "High-dose cyclophosphamide for graft-versus-host disease prevention" Current Opinion in Hematology,2010, 17:493-499.

Luznik, L. et al. "High-dose, post-transplantation cyclophosphamide to promote graft-host tolerance after allogeneic hematopoietic stem cell transplantation" Immunol Res, 2010, 47:65-77.

Luznik, L. et al. "HLA-Haploidentical Bone Marrow Transplantation for Hematologic Malignancies Using Nonmyeloablative Conditioning and High-Dose, Posttransplantation Cyclophosphamide" Biol Blood Marrow Transplant, Jun. 2008, 14(6):641-650.

Luznik, L. et al. "Nonmyeloablative alternative donor transplants" Current Opinion in Oncology, 2003, 15:121-126.

Luznik, L. et al. "Posttransplantation Cyclophosphamide Facilitates Engraftment of Major Histocompatibility Complex-Identical Allogeneic Marrow in Mice Conditioned With Low-Dose Total Body Irradiation" Biology of Blood and Marrow Transplantation, 2002, 8:131-138.

Luznik, L. et al. "Post-transplantation high dose cyclophosphamide (CY) is effective single agent for prevention of acute and chronic graft versus host disease after myeloablative HLA matched related and unrelated bone marrow transplantation (BMT)" Blood (ASH Annual Meeting Abstracts), 2008, 112: Abstract 56.

Magni, M. et al. "Induction of cyclophosphamide-resistance by aldehyde-dehydrogenase gene transfer" Blood, 1996, 87:1097-1103.

Maki, P.A. et al. "Potentiation of the Cytotoxic Action of Mafosfamide by N-Isopropyl-p-formylbenzamide, a Metabolite of Procarbazine" Cancer Research, Aug. 15, 1991, 51:4170-4175.

Mayumi, H. et al. "Cyclophosphamide-Induced Immunological Tolerance: an Overview" Immunobiol., 1996, 195:129-139.

Mayumi, H. et al. "Drug-Induced Tolerance to Allografts in Mice" Transplantation, 1987, 44(2):286-290.

McGuire, T.R. et al., "High-dose Cyclophosphamide in multiple sclerosis patients undergoing autologous stem cell transplantation," International Immunopharmacology, 3:279-283 (2003).

Mentzer, W.C. et al. "Availability of Related Donors for Bone Marrow Transplantation in Sickle Cell Anemia" Am. J. Pediatr. Hematol. Onco., 1994, 16(1):27-29.

Mielcarek, M. et al. "Graft-versus-host disease after nonmyeloablative versus conventional hematopoietic stem cell transplantation" Blood, Jul. 15, 2003, 102(2):756-762.

Mink, S.A. et al. "High-Dose Therapy in Lymphomas: A Review of the Current Status of Allogeneic and Autologous Stem Cell Transplantation in Hodgkin's Disease and Non-Hodgkin's Lymphoma" The Oncologist, 2001, 6:247-256.

(56) References Cited

OTHER PUBLICATIONS

Moreb, J.S. et al. "Retinoic Acid Down-Regulates Aldehyde Dehydrogenase and Increases Cytotoxicity of 4-Hydroperoxycyclophosphamide and Acetaldehyde" JPET, 2005, 312(1):339-345.

Moyo, Victor M., et al. "High-dose cyclophosphamide for refractrory autoimmune hemolytic anemia," Blood, 100(2) :704-706 (Jul. 15, 2002), XP-002430101.

Noonan, K. et al. "Enrichment of Allogeneic Tumor Antigen-Specific T Cells From Bone Marrow (BM) of Patients Treated with High-Dose Post-Transplant Cyclophoshamide (Cy)—A Novel Approach to Adoptive Immunotherapy" *Blood (ASH Annual Meeting Abstracts)*, 2011, 118: Abstract 647.

Nousari, Carlos, H., et al.; "Evaluating the role of immunoablative high-dose cyclophosphamide therapy in pemphigus vulgaris," Journal of the American Academy of Dermatology; vol. 49, No. 1, Jul. 2003; pp. 148-150, XP002430103 (ISSN: 0190-9622).

Nousari, Hossein C., et al., "Immunoablative high-dose cyclophosphamide without stem cell rescue in paraneoplastic pemphigus: Report of a case and review of this new therapy for severe autoimmune disease," Journal of the American Academy of Dermatology, 40(5):750-754 (May 1999).

O'Donnell, P. et al. "Favorable Outcome of Patients with Relapsed Hodgkin Lymphoma (HL) after Nonmyeloablative Hematopoietic Cell Transplation (NM-HCT) Using Related Haploidentical Donors" *Blood(ASH Annual Meeting Abstracts)*, 2006, 108:Abstract 3135.

O'Donnell, P.V. et al. "Nonmyeloablative Bone Marrow Transplantation from Partially HLA-Mismatched Related Donors Using Posttransplantation Cyclophosphamide" *Biology of Blood and Marrow Transplantation*, 2002, 8:377-386.

Openshaw, H. et al. "Peripheral Blood Stem Cell Transplantation in Multiple Sclerosis With Busulfan and Cyclophosphamide Conditioning: Report of Toxicity and Immunological Monitoring" *Biology of Blood and Marrow Transplantation*, 2000, 6:563-575.

Panepinto, J.A. et al. "Matched-related donor transplantation for sickle cell disease: report from the Center for International Blood and Transplant Research" *British Journal of Haematology*, 2007, 137:479-485.

Perini, P. et al., "Cyclophosphamide is effective in stablizing rapidly deteriorating secondary progressive multiple sclerosis," J Neurol 250:834-838 (2003).

Perry, J.J. et al. "Administration and pharmacokinetics of high-dose cyclophosphamide with hemodialysis support for allogeneic bone marrow transplantation in acute leukemia and end-stage renal disease" *Bone Marrow Transplantation*, 1999, 23:839-842.

Peters, W.P. et al. "High-Dose Combination Alkylating Agents With Bone Marrow Support as Initial Treatment for Metastatic Breast Cancer" *J Clin Oncol*, Sep. 1988, 6(9):1368-1376.

Petrus, M.J. et al. "An Immunoablative Regimen of Fludarabine and Cyclophosphamide Prevents Fully MHC-Mismatched Murine Marrow Graft Rejection Independent of GVHD" *American Society for Blood and Marrow Transplantation*, 2000, pp. 182-189.

Povsic, T.J. et al. "Circulating Progenitor Cells Can Be Reliably Identified on the Basis of Aldehyde Dehydrogenase Activity" JACC, Dec. 4, 2007, 50(23):2243-2248.

Prestrud, A.A. et al., "High-dose Cyclophosphamide Therapy Without Stem Cell Rescue for Severe Refractory Autoimmune Illnesses: Comment on the Article by Moore et al." Arthritis & Rheumatism, 48(5):1461-1470 (2003).

Rekha, G.K. et al. "Multienzyme-mediated stable and transient multidrug resistance and collateral sensitivity induced by xenobiotics" Cancer Chemother Pharmacol, 1997, 40:215-224.

Rossi, H.A. et al. "High-dose cyclophosphamide, BCNU, and VP-16 (CBV) conditioning before allogeneic stem cell transplantation for patients with non-Hodgkin's lymphoma". *Bone Marrow Transplantation*, 2003, 31:441-446.

Rother, R.P. et al. "Discovery and development of the complement inhibitor eculizumab for the treatment of paroxysmal nocturnal hemoglobinuria" *Nature Biotechnology*, Nov. 2007, 25(11):1256-1264.

Ruggieri, M. et al. "Glatiramer Acetate in Multiple Sclerosis: A Review" *CNS Drug Reviews*, 2007, 13(2):178-191.

Russo, J.E. et al. "Characterization of Cytosolic Aldehyde Dehydrogenase from Cyclophosphamide Resistant L1210 Cells" Cancer Res, Jun. 1, 1988, 48:2963-2968.

Safety Data Sheet "Cyclosphosphamide" Division of Occupational Health and Safety National Institutes of Health, prepared by the Environmental Control and Research Program, Mar. 1987, 8 pages.

Sahovic, E.A. et al. "Role for Aldehyde Dehydrogenase in Survival of Progenitors for Murine Blast Cell Colonies after Treatment with 4-Hydroperoxycyclophosphamide in Vitro" Cancer Research, Mar. 1, 1988, 48:1223-1226.

Santos, G. W. et al.; "The Use of Cyclo Phosphamide for Clinical Marrow Transplantation," Transplantation Proceedings, vol. 4, No. 4, 1972, pp. 559-564, XP009082012 (ISSN: 0041-1345).

Savage, W.J. et al. "Treatment of Hepatitis-Associated Aplastic Anemia with High Dose Cyclophosphamide," ASH 2006, Session Type: Poster Session, Board #103-I; Abstract 179, (Dec. 9, 2006); Abstract 975 appears in Blood, vol. 108, issue 11, (Nov. 16, 2006).

Schwartzman, R.J. et al., "High-Dose Cyclophosphamide in the Treatment of Multiple Sclerosis," Neuroscience & Therapeutics 15:118-127 (2009).

Sehgal et al., "Infectious Complications of High-Dose Cyclophosphamide Treatment in Autoimmune Disease," Blood (ASH Annual Meeting Abstracts), 104:Abstract 5091 (2004).

Shammo, J. et al., "Immune Ablation Using High-Dose Cyclophosphamide without Stem Cell Rescue for Intractable Multiple Sclerosis," Blood (ASH Annual Meeting Abstacts) 106: Abstract 5504 (2005).

Shih, W.W.H. et al. "Difference in effect of single immunosuppressive agents (cyclophosphamide, CCNU, 5-FU) on peripheral blood immune cell parameters and central nervous system immunoglobulin synthesis rate in patients with multiple sclerosis" Clin. Exp. Immunol., 1983, 53:122-132.

Sládek, N. E. et al. "Aldehyde Dehydrogenase-Mediated Cellular Relative Insensitivity to the Oxazaphosphorines" Curr. Pharm. Des., 1999, 5(8):607-625.

Sládek, N. E. et al. "Cellular levels of aldehyde dehydrogenases (ALDH1A1 and ALDH3A1) as predictors of therapeutic responses to cyclophosphamide-based chemotherapy of breast cancer: a retrospective study" Cancer Chemother Pharmacol, 2002, 49:309-321.

Sládek, N. E. et al. "Human Aldehyde Dehydrogenases: Potential Pathological, Pharmacological, and Toxicological Impact". J. Biochem. Molecular Toxicology, 2003, 17(1):7-23.

Smith, D. R., et al.: "A randomized blinded trial of combination therapy with cyclophosphamide in patients with active multiple sclerosis on interferon beta" Multiple Sclerosis, vol. 11, No. 5, Oct. 2005, pp. 573-582, XP009082240 (ISSN: 1352-4585).

Snowden, J.A. "Haemopoetic Stem Cell Transplantation in Autoimmune Disease" Bangkok, Thailand, Oct. 24-28, 1999, pp. 180-183.

Spitzer, T.R. "Nonmyeloablative Allogeneic Stem Cell Transplant Strategies and the Role of Mixed Chimerism" *The Oncologist*, 2000, 5:215-223.

Sreerama, L. et al. "Cellular Levels of Class 1 and Class 3 Aldehyde Dehydrogenases and Certain Other Drug-metabolizing Enzymes in Human Breast Malignancies" Clinical Cancer Research, Nov. 1997, 3:1901-1914.

Sreerama, L. et al. "Identification of a Class 3 Aldehyde Dehydrogenase in Human Saliva and Increased Levels of this Enzyme, Glutathione S-Transferases, and DT-Diaphorase in the Saliva of Subjects Who Continually Ingest Large Quantities of Coffee or Broccoli" Clin Cancer Res, Oct. 1995, 1:1153-1163.

Sreerama, L. et al. "Identification of a Methylcholanthrene-induced Aldehyde Dehydrogenase in a Human Breast Adenocarcinoma Cell Line Exhibiting Oxazaphorine-specific Acquired Resistance" Cancer Res, Apr. 15, 1994, 54:2176-2185.

Storb, R. et al. "Marrow Transplantation From HLA-Identical Siblings for Treatment of Aplastic Anemia: Is Exposure to Marrow Donor Blood Products 24 Hours Before High-Dose Cyclophosphamide Needed for Successful Engraftment?" *Blood*, Apr. 1983, 61(4):672-675.

Swinnen L.J. et al., "Phase II Study of High Dose Outpatient Cyclophosphamide and Rituximab, without Stem Cell Support, for

(56) References Cited

OTHER PUBLICATIONS

Low Grade and Mantle Cell Lymphoma," ASH 2006, Session Type: Poster Session, Board #919-II; Abstract 2741, (Dec. 10, 2006); Abstract 2741 appears in Blood, vol. 108, issue 11, (Nov. 16, 2006).
Symons, H. et al. "HLA-Haploidentical Bone Marrow Transplantation (BMT) for High Risk Hematologic Malignancies Using Myeloablative Conditioning and High-Dose, Posttransplantation Cyclophosphamide" *Blood (ASH Annual Meeting Abstracts)*, 2010, 116: Abstract 2362.
Symons, H.J. et al. "Impact of Killer Immunoglobulin Receptor (KIR) Ligand Incompatibility in Nonmyeloablative Bone Marrow Transplantation (BMT) from Haploidentical Donors" *Blood (ASH Annual Meeting Abstracts)*, 2006, 108: Abstract 604.
Symons, H.J. et al. "Improved survival with inhibitory Killer Immunoglobulin Receptor (KIR) gene mismatches and KIR haplotype B donors after nonmyeloablative, HLA-haploidentical bone marrow transplantation" *Biol Blood Marrow Transplant,* Apr. 2010, 16(4):533-542.
Symons, H.J. et al. "Low Incidence of CMV Reactivation and Infectious Morbidity and Mortality after Nonmyeloablative Haploidentical Bone Marrow Transplantation Incorporating Post-Transplantation Cyclophosphamide" *Blood (Ash Annual Meeting Abstracts)*, 2005, 106: Abstract 3245.
Symons, H.J. et al. "Low Incidence of CMV Reactivation and Infection after Allogeneic Bone Marrow Transplantation (BMT) Incorporating Post-Transplantation Cyclophosphamide (Cy)" *Blood (ASH Annual Meeting Abstracts)*, 2006, 108: Abstract 2859.
Takahashi, Y. et al. "In vitro and in vivo evidence of PNH cell sensitivity to immune attack after nonmyeloablative allogeneic hematopoietic cell transplantation" *Blood,* Feb. 15, 2004, 103(4):1383-1390.
Takebe, N. et al. "Generation of Dual Resistance to 4-Hydroperoxycyclophosphamide and Methotrexate by Retroviral Transfer of the Human Aldehyde Dehydrogenase Class 1 Gene and a Mutated Dihydrofolate Reductase Gene" Molecular Therapy, Jan. 2001, 3(1):88-96.
Today's Sunbeam Article, "For Pennsville woman with MS, new treatment has been 'just a miracle," post Apr. 25, 2004.
Toze, C.L. et al. "Myeloablative allografting for chronic lymphocytic leukemia: evidence for a potent graft-versus-leukemia effect associated with graft-versus-host disease" *Bone Marrow Transplantation,* 2005, 36:825-830.
USA Today Article, "Researchers say large doses of chemo drug may fight MS," Posted Mar. 23, 2004.
Van Besien, K. et al. "Fludarabine-based conditioning for allogeneic transplantation in adults with sickle cell disease" *Bone Marrow Transplantation,* 2000, 26:445-449.
Venkataranganna, M.V. et al. "Pharmacodynamics & toxicological profile of PartySmart, a herbal preparation for alcohol hangover in Wistar rats" Indian J Med Res, May 2008, 127:460-466.
Vose, J.M. "Single Dose Pegfilgrastin (SD/01) Is as Effective as Daily Filgrastim Following ESHAP Chemotherapy for Subjects with Non-Hodgkin's Lymphoma or Hodgkin's Disease: Results of a Randomized, Open-Label Study" OncoLink Scientific Meetings Coverage, held Tuesday, Dec. 11, 2001, retrieved from http://www.oncolink.org/conferences/article.cfm?id=490.
Walters, M.C. "Cord blood transplantation for sickle cell anemia: Bust or boom?" *Pediatr Transplantation,* 2007, 11:582-583.
Weiner, H. L., et al.; "Treatment of multiple sclerosis with cyclophosphamide: Critical review of clinical and immunologic effects," Multiple Sclerosis, vol. 8, No. 2, Apr. 2002, pp. 142-154, XP009082459 (ISSN: 1352-4585).
Zhang, J. et al. "Clinical Pharmacology of Cyclophosphamide and Ifosfamide" Current Drug Therapy, 2006, 1:55-84.
Zhou, X. et al. "Synergy between Nonmyeloablative Doses of Intravenous Busulfan and Post-Transplantation Cyclophosphamide for Induction of Tolerance to MHC-Compatible Stem Cell Allografts" *Blood, (Ash Annual Meeting Abstracts)*, 2005, 106: Abstract 3040.
Zoumbos, N. C. et al. "Circulating Activated Suppressor T Lymphocytes in Aplastic Anemia" *The New England Journal of Medicine,* Jan. 31, 1985, 312(5):257-265.
Leandro et al., "An Open Study of B Lymphocyte Depletion in Systemic Lupus Erythematosus," Arthritis & Rheumatism, 46(10):2673-2677 (2002).
International Search Report dated Jun. 10, 2009 in International Application Serial No. PCT/US2008/084396, filed Nov. 21, 2008.
International Search Report dated Jun. 25, 2009 in International Application Serial No. PCT/US2008/084414, filed Nov. 21, 2008.
International Search Report dated Jun. 7, 2007, from PCT/US2006/061549.
International Search Report dated Nov. 6, 2008, from PCT/US2007/078518.
International Search Report dated Jan. 29, 2009, from PCT/US2007/078521.
International Search Report dated Jan. 8, 2009, from PCT/US2007/078524.
International Search Report dated Dec. 24, 2008, from PCT/US07/81614.
Supplementary European Search Report dated Apr. 27, 2011 from EP 11 00 1548.

* cited by examiner

CYCLOPHOSPHAMIDE IN COMBINATION WITH ANTI-IDIOTYPIC VACCINES

CROSS-REFERENCE TO RELATED APPLICATIONS

The present application is a continuation of U.S. Ser. No. 13/017,817 filed on Jan. 31, 2011, now abandoned, which is a continuation of U.S. Ser. No. 12/818,380 filed on Jun. 18, 2010, now abandoned, which is a continuation of U.S. Ser. No. 12/610,798 filed on Nov. 2, 2009, now abandoned, which is a continuation of U.S. Ser. No. 12/404,891 filed on Mar. 16, 2009, now abandoned, which is a continuation of PCT/US2007/078521 filed on Sep. 14, 2007, which claims priority to U.S. Ser. No. 60/844,830 filed on Sep. 15, 2006.

BACKGROUND

Surgery, chemotherapy and radiation therapy are the mainstay of cancer treatment and management. Surgery and radiation therapy are typically used to achieve results locally, whereas chemotherapy exerts a more systemic effect. Low to intermediate doses of cyclophosphamide are routinely used in combination chemotherapy for treating various types of cancers and appears to work either by stopping the growth of cancer cells or by killing the cancer cells. However, usually remaining cancer cells are able to divide, thereby leading to a relapse of the cancer. Accordingly, despite the use of combination chemotherapy to treat various types of cancers, a significant number of cancers remain incurable.

More recently, immunotherapy based techniques have been developed for the treatment of various cancers. The central premise underlying immunotherapy for cancer is the presence of antigens which are selectively or abundantly expressed or mutated in cancer cells. For example, active immunotherapy involves delivering an antigen associated with a cancer to a patient, such that the patient's immune system elicits an immune response against the antigen and consequently, against the cancer cells expressing the antigen. Passive immunotherapy, on the other hand, involves administering immune therapeutics such as, for example, an antibody which selectively binds an antigen expressed on a cancer cell.

Despite the advances in the development of various immune therapies for treatment of cancer, immune tolerance presents a major barrier. Therefore, there is a need to identify therapies or agents which may be used to break immune tolerance which severely limits the use of various immune therapies in cancer therapy.

SUMMARY

This invention is based, at least on part, on the discovery that, high-dose cyclophosphamide is effective in breaking immune tolerance which presents a barrier in the use of various immune based therapeutics in the treatment of cancer. The present invention provides methods of treating various cancers and, in particular, B-cell derived cancers, such as, for example, non-Hodgkin's lymphoma, Hodgkin's lymphoma, chronic lymphocytic leukemia, mantle cell lymphoma or multiple myeloma, using high-dose pulsed amount of an oxazaphosphorine drug such as, for example, cyclophosphamide, in combination with an immune therapeutic such as, for example, an autologous anti-idiotypic vaccine.

In yet another aspect, the oxazaphosphorine drug is powdered cyclophosphamide or a pharmaceutically acceptable salt, solvate, prodrug, or metabolite thereof.

In still another aspect, the oxazaphosphorine drug is lyophilized cyclophosphamide or a pharmaceutically acceptable salt, solvate, prodrug, or metabolite thereof.

In one aspect of the present invention, a method of eliminating or substantially reducing non-Hodgkin's lymphoma in a subject is provided. The method includes administering a lymphocytotoxic but hematopoeitic stem cell sparing high-dose pulsed amount of an oxazaphosphorine drug to the subject, such that the subject's immune system reconstitutes without stem cell transplantation, and administering an effective amount of an autologous anti-idiotypic tumor vaccine, thereby to eliminate or substantially reduce non-Hodgkin's lymphoma in the subject.

In another aspect of the present invention, a method of eliminating or substantially reducing Hodgkin's lymphoma in a subject is provided. The method includes administering a lymphocytotoxic but hematopoeitic stem cell sparing high-dose pulsed amount of an oxazaphosphorine drug to the subject, such that the subject's immune system reconstitutes without stem cell transplantation, and administering an effective amount of an autologous anti-idiotypic tumor vaccine, thereby to eliminate or substantially reduce non-Hodgkin's lymphoma in the subject.

In yet another aspect of the present invention, a method of eliminating or substantially reducing chronic lymphocytic leukemia (CLL) in a subject is provided. The method includes administering a lymphocytotoxic but hematopoeitic stem cell sparing high-dose pulsed amount of an oxazaphosphorine drug to the subject, such that the subject's immune system reconstitutes without stem cell transplantation, and administering an effective amount of an autologous anti-idiotypic tumor vaccine, thereby to eliminate or substantially reduce chronic lymphocytic leukemia in the subject.

In a further aspect of the present invention, a method of eliminating or substantially reducing mantle cell lymphoma in a subject is provided. The method includes administering a lymphocytotoxic but hematopoeitic stem cell sparing high-dose pulsed amount of an oxazaphosphorine drug to the subject, such that the subject's immune system reconstitutes without stem cell transplantation, and administering an effective amount of an autologous anti-idiotypic tumor vaccine, thereby to eliminate or substantially mantle cell lymphoma in the subject.

In yet another aspect of the present invention, a method of eliminating or substantially reducing multiple myeloma in a subject is provided. The method includes administering a lymphocytotoxic but hematopoeitic stem cell sparing high-dose pulsed amount of an oxazaphosphorine drug to the subject, such that the subject's immune system reconstitutes without stem cell transplantation, and administering an effective amount of an autologous anti-idiotypic tumor vaccine, thereby to eliminate or substantially reduce multiple myeloma in the subject.

In one or more aspects of the present invention, a method for eliminating or substantially reducing non-Hodgkin's lymphoma or Hodgkin's lymphoma or chronic lymphocytic leukemia, mantle cell lymphoma or multiple myeloma further includes administration of an effective amount of granulocyte-monocyte colony stimulating factor (GM-CSF). In some embodiments, GM-CSF is administered in conjunction with an autologous anti-idiotypic vaccine.

In another aspect of the present invention, a method for eliminating or substantially reducing a B-cell derived cancer selected from the group consisting of non-Hodgkin's lymphoma, Hodgkin's lymphoma, chronic lymphocytic leukemia, mantle cell lymphoma and multiple myeloma is provided. The method includes administering an effective amount of an antibody that selectively binds a B-cell specific antigen, followed by, administering a lymphocytotoxic high-dose pulsed amount of an oxazaphosphorine drug to the subject, such that the subject's immune system reconstitutes without stem cell transplantation, and, followed by, administering an autologous anti-idiotype anti-tumor vaccine in conjunction with granulocyte-monocyte colony stimulating factor to the subject, thereby to eliminate or substantially reduce the B-cell derived cancer.

An antibody used in the methods of the invention may selectively bind an antigen chosen from: CD3d, CD5, CD6, CD9, CD19, CD20, CD21, CD22, CD23, CD24, CD27, CD28, CD37, CD38, CD40, CD45, CD46, CD48, CD53, CD69, CD70, CD72, CD73, CD79a, CD79b, CD80, CD81, CD83, CD85a, CD85d, CD85e, CD85h, CD85i, CD85j, CD85k, CD86, CD96, CD98, CD100, CD121b, CD124, CD127, CD132, CD150, CD152, CD154, CD157, CD166, CD169, CD179a, CD179b, CD180, CD185, CD196, CD197, CD205, CDw210a, CD213a1, CD257, CD267, CD268, CD269, CD274, CD275, CD276, CD278, CD279, CD300a, CD300c, CD307, CD314, CD316, CD317, CD319, CD320, CDw327, or CD331.

In some embodiments, an antibody used in the methods of the invention is a monoclonal antibody that selectively binds CD-20. In other embodiments, an antibody used in the methods of the invention is a monoclonal antibody that selectively binds CD-22. In yet other embodiments, both an antibody that selectively binds CD-20 and an antibody that selectively binds CD-22 are administered to a subject having non-Hodgkin's lymphoma, Hodgkin's lymphoma, chronic lymphocytic leukemia, mantle cell lymphoma or multiple myeloma. In some embodiments, one or more antibodies that selectively bind a B-cell specific antigen are administered to a subject having non-Hodgkin's lymphoma or Hodgkin's lymphoma or chronic lymphocytic leukemia, mantle cell lymphoma or multiple myeloma, in conjunction with a lymphocytotoxic but hematopoeitic cell sparing high-dose pulsed amount of an oxazaphosphorine drug and an effective amount of an autologous anti-idiotypic vaccine and optionally, an effective amount of GM-CSF.

In some embodiments of the present invention, an effective amount of a monoclonal antibody that selectively binds a B-cell specific antigen is between about 100 mg/m$^2$ to about 200 mg/m$^2$. In other embodiments of the present invention, an effective amount of a monoclonal antibody that selectively binds a B-cell specific antigen is between about 200 mg/m$^2$ to about 300 mg/m$^2$, or between about 300 mg/m$^2$ to about 400 mg/m$^2$. In a particular embodiment, an effective amount of a monoclonal antibody that selectively binds a B-cell specific antigen is about 375 mg/m$^2$.

In some other embodiments, a lymphocytotoxic but hematopoeitic cell sparing high-dose pulsed amount of an oxazaphosphorine drug used in the methods described herein is between 100 mg/kg and 200 mg/kg, administered daily from 1 to 7 days. In other embodiments, a lymphocytotoxic but hematopoeitic cell-sparing high-dose pulsed amount of an oxazaphosphorine drug is between 25 mg/kg and 100 mg/kg, administered daily for 4 consecutive days. In some embodiments, a lymphocytotoxic but hematopoeitic stem cell sparing high-dose pulsed amount of an oxazaphosphorine drug is administered to the subject for 4 days. In other embodiments, a lymphocytotoxic but hematopoeitic stem cell sparing high-dose pulsed amount of an oxazaphosphorine drug is 50 mg/kg/day, administered for 4 days.

In various embodiments of the methods of the present invention, the oxazaphosphorine drug is selected from the group consisting of cyclophosphamide, ifosfamide, perfosfamide, trophosphamide (trofosfamide), or a pharmaceutically acceptable salt, solvate, prodrug and metabolite thereof. In some embodiments, an oxazaphosphorine drug used in the methods described herein is cyclophosphamide or a pharmaceutically acceptable salt or metabolite thereof.

Also encompassed by this disclosure is a kit for treating non-Hodgkin's lymphoma, Hodgkin's lymphoma, chronic lymphocytic leukemia, mantle cell lymphoma or multiple myeloma including: (a) a plurality of doses of a lymphocytotoxic but hematopoetic cell-sparing high-dose pulsed amount of a oxazaphosphorine drug; (b) a plurality of doses of an effective amount of an autologous anti-idiotypic vaccine; and optionally, (c) one or more monoclonal antibodies that selectively bind a B-cell specific antigen; and (c) instructions for treating non-Hodgkin's lymphoma, Hodgkin's lymphoma, chronic lymphocytic leukemia, mantle cell lymphoma or multiple myeloma, where the non-Hodgkin's lymphoma, Hodgkin's lymphoma, chronic lymphocytic leukemia, mantle cell lymphoma or multiple myeloma disorder is treated without the need for stem cell transplantation.

In certain aspects, the methods of the invention further comprise administering an effective amount of Mesna.

DETAILED DESCRIPTION

I. Definitions

In order that the present disclosure may be more readily understood, certain terms are first defined. Additional definitions are set forth throughout the detailed description.

The term "an oxazaphosphorine drug" refers to a class of drugs which act as alkylating agents and cause immunoablation. They are generally highly cytotoxic and are often used as chemotherapeutic agents. Examples of oxazaphosphorine drugs include cyclophosphamide, ifosfamide, perfosfamide, trophosphamide (trofosfamide), and pharmaceutically acceptable salts, solvates, prodrugs and metabolites thereof In some embodiments, an oxazaphosphorine drug used in the methods described herein is cyclophosphamide, which is sold under common trade-names including PROCYTOX®, CYTOXAN® and NEOSAR®. Cyclophosphamide is converted to 4-hydroxycyclophosphamide and its tautomer aldophosphamide in the liver and is cytotoxic to cells that express low levels of the enzyme aldehyde dehydrogenase, for example, NK cells and T and B lymphocytes. Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents which are structurally related to cyclophosphamide. For example, Perfosfamide alkylates DNA, thereby inhibiting DNA replication and RNA and protein synthesis.

As used herein, the phrase "high-dose pulsed amount of an oxazaphosphorine drug" refers to a non-myeloablative amount of an oxazaphosphorine drug such as, for example, cyclophosphamide, which is immunoablative, upon single or multiple dose administration to a subject (such as a human patient suffering from non-Hodgkin's lymphoma, Hodgkin's lymphoma, chronic lymphocytic leukemia, mantle cell lymphoma or multiple myeloma), thereby resulting in a substantial reduction in or complete elimination of mature circulating lymphocytes in the subject. In some embodiments, administration of a non-myeloablative amount of cyclophosphamide in combination with one or more immune therapeutics described herein results in treating, preventing, curing, delaying, reducing the severity of, ameliorating at least one symptom of non-Hodgkin's lymphoma, Hodgkin's lymphoma, chronic lymphocytic leukemia, mantle cell lymphoma or multiple myeloma, or prolonging the survival of the subject beyond that expected in the absence of such administration. In some embodiments, "high-dose pulsed amount of an oxazaphosphorine drug" refers to a dose of cyclophosphamide administered to a subject in need thereof, which results in eliminating or substantially reducing the number of circulating lymphocytes in the subject, including those which are associated with immune tolerance associated with cancer, while sparing the hematopoeitic progenitor stem cells. For example, in some embodiments, "high-dose pulsed amount of an oxazaphosphorine drug" is a 50 mg/kg/day dose of an oxazaphosphorine drug such as, for example, cyclophosphamide, administered to a subject in need thereof for 4 consecutive days.

The terms "eliminating," "substantially reducing," "treating," and "treatment," as used herein, refer to therapeutic or preventative measures described herein. The methods of "eliminating or substantially reducing" employ administration to a subject having non-Hodgkin's lymphoma, Hodgkin's lymphoma, chronic lymphocytic leukemia, mantle cell lymphoma or multiple myeloma, a lymphocytotoxic non-myeloablative amount of an oxazaphosphorine drug such as, for example, cyclophosphamide, in combination with immune therapeutics such as, monoclonal antibodies and/or autologous anti-idiotypic vaccines, such as to prevent, cure, delay, reduce the severity of, or ameliorate one or more symptoms of non-Hodgkin's lymphoma, Hodgkin's lymphoma, chronic lymphocytic leukemia, mantle cell lymphoma or multiple myeloma disorder, thereby prolonging the survival of a subject beyond that expected in the absence of such treatment. In some embodiments, the term "eliminating" refers to a complete remission of a cancer, e.g., non-Hodgkin's lymphoma, Hodgkin's lymphoma, chronic lymphocytic leukemia, mantle cell lymphoma or multiple myeloma in a subject treated using the methods described herein.

The term "hematopoeitic progenitor stem cell," as used herein refers to any type of cell of the hematopoeitic system, including, but not limited to, undifferentiated cells such as hematopoeitic stem cells and progenitor cells, which are capable of reconstituting the immune system following administration of a lymphocytotoxic non-myeloablative amount of cyclophosphamide to a subject having a B-cell derived cancer such as, for example, non-Hodgkin's lymphoma, Hodgkin's lymphoma, mantle cell lymphoma, chronic lymphocytic leukemia or multiple myeloma.

The terms "B lymphocyte" and "B cell," as used interchangeably herein, are intended to refer to any cell within the B cell lineage as early as B cell precursors, such as pre-B cells B220$^+$ cells which have begun to rearrange Ig VH genes and up to mature B cells and even plasma cells such as, for example, plasma cells which are associated with multiple myeloma. The term "B-cell," also includes a B-cell derived cancer stem cell, i.e., a stem cell which is capable of giving rise to non-Hodgkin's lymphoma, Hodgkin's lymphoma, chronic lymphocytic leukemia, mantle cell lymphoma or multiple myeloma. Such cells can be readily identified by one of ordinary skill in the art using standard techniques known in the art and those described herein.

The terms "immunoablation" and "immunoablative," as used herein, refer to severe immunosuppression using a high-dose (i.e., lymphocytotoxic non-myeloablative amount) of cyclophosphamide, for example, 50 mg/kg×4 days of cyclophosphamide, which leads to substantial reduction in or elimination of the population of circulating lymphocytes, including for example, NK cells and B and T lymphocytes Immunoablation, as described herein, results in complete or substantially complete reduction in immune cells responsible for immune tolerance.

The term "lymphocytotoxic," as used herein, refers to complete elimination of or substantial reduction in the number of circulating lymphocytes, including those associated with immune tolerance in a subject following administration of a high-dose (i.e., lymphocytotoxic non-myeloablative amount) of a oxazaphosphorine drug, such as, for example, 50 mg/kg×4 days of cyclophosphamide. The term "lymphocytotoxic," includes killing of those immune cells by cyclophosphamide which express low levels of the enzyme aldehyde dehydrogenase.

The term "non-myeloablative," as used herein, refers to a property of a compound such as, for example, an oxazaphosphorine drug such as cyclophosphamide, whereby the compound does not have a cytotoxic effect on myeloid cells, for example, hematopoeitic progenitor stem cells. In some embodiments, a non-myeloablative agent used in the methods described herein has a cytotoxic effect on the circulating mature lymphocytes (e.g., NK cells, and T and B lymphocytes) while sparing the progenitor cells, e.g., hematopoeitic progenitor stem cells that are capable of reconstituting the immune system. In some embodiments, a non-myeloablative agent used in the methods of the invention kills cells which express low levels of the enzyme aldehyde dehydrogenase (e.g., NK cells and B and T lymphocytes) while sparing cells which express high or resistant levels of the enzyme aldehyde dehydrogenase (e.g., hematopoeitic progenitor stem cells).

The term "immune tolerance," as used herein, refers to a condition in which an animal recognizes a particular cell or antigen(s) as self, which should be recognized as foreign. In other words, the animal's immune system fails to mount an immune response to a cell or antigen(s) because the antigen is recognized as self instead of foreign. For example, the animal fails to mount an immune response against an antigen which is specifically expressed on a cancer cell.

The terms "immunoglobulin" and "antibody" (used interchangeably herein) include a protein having a basic four-polypeptide chain structure consisting of two heavy and two light chains, said chains being stabilized, for example, by interchain disulfide bonds, which has the ability to specifically bind an antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind an antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable," based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions." The "constant" domains of an antibody light chain are referred to interchangeably as "light chain constant regions," "light chain constant domains," "CL" regions or "CL" domains. The "constant" domains of an antibody heavy chain are referred to interchangeably as "heavy chain constant regions," "heavy chain constant domains," "CH" regions or "CH" domains). The "variable" domains of an antibody light chain are referred to interchangeably as "light chain variable regions," "light chain variable domains," "VL" regions or "VL" domains). The "variable" domains of an antibody heavy chain are referred to interchangeably as "heavy chain constant regions," "heavy chain constant domains," "VH" regions or "VH" domains).

Immunoglobulins or antibodies can exist in monomeric or polymeric form, for example, IgM antibodies which exist in pentameric form and/or IgA antibodies which exist in monomeric, dimeric or multimeric form. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) *Clin. Exp. Immunol.* 79:315-321; Kostelny et al., (1992) *J. Immunol.* 148:1547-1553.

The term "antigen-binding portion" of an antibody (or "antibody portion") includes fragments of an antibody that retain the ability to specifically bind to an antigen (e.g., a B-cell specific antigen). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al., (1993) *Proc. Natl. Acad. Sci. USA* 90:6444-6448; Poljak, R. J. et al., (1994) *Structure* 2:1121-1123). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M. et al., (1995) *Human Antibodies and Hybridomas* 6:93-101) and use of a cysteine residue, a marker peptide and a C-terminal polyhistidine tag to make bivalent and biotinylated scFv molecules (Kipriyanov, S. M. et al., (1994) *Mol. Immunol.*, 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Preferred antigen binding portions are complete domains or pairs of complete domains.

"Specific binding," "specifically binds," "selective binding," and "selectively binds," as used herein, mean that the compound, e.g., antibody or antigen-binding portion thereof, exhibits appreciable affinity for a particular antigen or epitope and, generally, does not exhibit significant cross-reactivity with other antigens and epitopes. "Appreciable" or preferred binding includes binding with an affinity of at least $10^6$, $10^7$, $10^8$, $10^9$ M$^{-1}$, or $10^{10}$ M$^{-1}$. Affinities greater than $10^7$M$^{-1}$, preferably greater than $10^8$ M$^{-1}$ are more preferred. Values intermediate of those set forth herein are also intended to be within the scope of the present invention and a preferred binding affinity can be indicated as a range of affinities, for example, $10^6$ to $10^{10}$ M$^{-1}$, preferably $10^7$ to $10^{10}$ M$^{-1}$, more preferably $10^8$ to $10^{10}$ M$^{-1}$. An antibody that "does not exhibit significant cross-reactivity" is one that will not appreciably bind to an undesirable entity (e.g., an undesirable proteinaceous entity). For example, in one embodiment, an antibody or antigen-binding portion thereof, that specifically binds to a B-cell specific antigen, such as, for example, CD-20 or CD-22, will appreciably bind CD-20 or CD-22, but will not significantly react with other non-CD-20 or non-CD-22 proteins or peptides. Specific or selective binding can be determined according to any art-recognized means for determining such binding, including, for example, according to Scatchard analysis and/or competitive binding assays.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The term "human antibody" includes antibodies having variable and constant regions corresponding to human germline immunoglobulin sequences as described by Kabat et al. (See Kabat, et al., (1991) *Sequences of proteins of Immunological Interest, Fifth Edition*, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In a preferred embodiment, these replacements are within the CDR regions as described in detail below.

The term "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D. et al., (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences (See Kabat E. A., et al., (1991) *Sequences of Proteins of Immunological Interest, Fifth Edition*, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities (e.g., an isolated antibody that specifically binds a B-cell specific antigen and is substantially free of antibodies or antigen-binding portions thereof that specifically bind other antigens, including other B-cell antigens). An isolated antibody that specifically binds a B-cell specific antigen may bind the same antigen and/or antigen-like molecules from other species. Moreover, an isolated antibody may be substantially free of other cellular material and/or chemicals.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The terms "idiotype," "Id," and "idiotypic determinant," as used herein, refer to an epitope in the hypervariable region of an immunoglobulin. Typically, an idiotype or an epitope thereof is formed by the association of the hypervariable or complementarity determining regions (CDRs) of VH and VL domains.

The terms "anti-idiotypic" and "anti-Id," refer to the binding of an antibody or antigen-binding portion thereof to one or more idiotypes.

The term "autologous anti-idiotypic vaccine" refers to a composition, the active ingredient of which is an immunogenic molecule capable of inducing an immune response against a B-cell idiotype derived from the same subject to which it is administered. In some embodiments, the immunogenic molecule in a vaccine used in the methods of the present invention is a normal product of a subject's B cells that happens to be expressed clonally on the cancer cells (e.g., cells derived from a Hodgkin's lymphoma or non-Hodgkin's lymphoma or chronic lymphocytic leukemia, mantle cell lymphoma or multiple myeloma) and serves as a unique a target for immune attack. In some embodiments, an "autologous anti-idiotypic vaccine," is capable of eliciting an immune response against a B-cell idiotype derived from a subject having non-Hodgkin's lymphoma. In another embodiment, an "autologous anti-idiotypic vaccine," is capable of eliciting an immune response against a B-cell idiotype derived from a subject having Hodgkin's lymphoma. In yet another embodiment, an "autologous anti-idiotypic vaccine," is capable of eliciting an immune response against a B-cell idiotype derived from a subject having chronic lymphocytic leukemia. In a further embodiment, an "autologous anti-idiotypic vaccine," is capable of eliciting an immune response against a B-cell idiotype derived from a subject having multiple myeloma. In a yet further embodiment, an "autologous anti-idiotypic vaccine," is capable of eliciting an immune response against a B-cell idiotype derived from a subject having mantle cell lymphoma. In some embodiments of the present invention, an "autologous anti-idiotypic vaccine," is used for the treatment of a B-cell derived cancer in combination with a lymphocytotoxic but hematopoeitic cell sparing high-dose pulsed amount of an oxazaphosphorine drug. In other embodiments of the present invention, an "autologous anti-idiotypic vaccine" is used for the treatment of a B-cell derived cancer in combination with other immune therapeutics such as, for example, monoclonal antibodies that selectively bind B-cell specific antigens. In some embodiments, an "autologous anti-idiotypic vaccine" includes an antigen associated with a B-cell derived cancer in a subject (e.g., non-Hodgkin's lymphoma, Hodgkin's lymphoma, chronic lymphocytic leukemia, mantle cell lymphoma or multiple myeloma) linked to KLH (keyhole limpet hemocyanin, a carrier protein). In some embodiments of the present invention, an autologous anti-idiotypic vaccine is administered with GM-CSF.

The term "granulocyte monocyte colony stimulating factor" or "GM-CSF" refers to a hematopoeitic growth factor that stimulates the development of committed progenitor cells to neutrophils and enhances the functional activities of neutrophils. It is produced in response to specific stimulation by a variety of cells including macrophages, fibroblasts, endothelial cells and bone marrow stroma. GM-CSF can be used clinically to facilitate hematopoeitic recovery after bone marrow transplantation. In some embodiments described herein, GM-CSF is administered to increase the neutrophil count to a level which falls within a normal range. Either purified GM-CSF or recombinant GM-CSF, for example, recombinant human GM-CSF (R & D SYSTEMS, INC, Minneapolis, Minn.) can be used in the methods described herein.

The phrase "an effective amount of granulocyte monocyte colony stimulating factor" refers to an amount of granulocyte monocyte colony stimulating factor, which upon a single or multiple dose administration to a subject, results in an elevation in neutrophil count in the subject. Elevation in neutrophil count includes any measurable increase in neutrophil count or appearance of neutrophils following administration of an effective amount of granulocyte monocyte colony stimulating factor. A measurable increase can be, for example, a 5-fold, or a 10-fold, or a 15-fold, or a 20-fold, or a 25-fold, or a 30-fold, or a 40-fold, or a 50-fold, or a 60-fold, or a 70-fold, or a 80-fold, or a 90-fold, or a 100-fold, or greater than a 100-fold increase in neutrophil count following administration of an effective amount of granulocyte monocyte colony stimulating factor. In some embodiments, an elevation in neutrophil count includes elevation to a count that is within a normal range, as understood by one of ordinary skill in the art. In some embodiments, "an effective amount of monocyte granulocyte colony stimulating factor" refers to a daily administration of 5 µg/kg of the granulocyte colony stimulating factor.

II. Exemplary Disorders

Exemplary disorders which may be treated using the methods of the invention include cancer and in particular, B-cell derived cancers such as, for example, non-Hodgkin's lymphoma, Hodgkin's lymphoma, chronic lymphocytic leukemia, mantle cell lymphoma and multiple myeloma. Additional B-cell derived cancers include, for example, B-cell prolymphocytic leukemia, lymphoplasmocytic leukemia, splenic marginal zone lymphoma, marginal zone lymphoma (extra-nodal and nodal), and follicular lymphoma (e.g., Grade I and II).

In some embodiments, a cancer treated using the methods of the present invention is a B-cell derived cancer associated with the expression of one or more B-cell specific antigens such as, for example, CD3d, CD5, CD6, CD9, CD19, CD20, CD21, CD22, CD23, CD24, CD27, CD28, CD37, CD38, CD40, CD45, CD46, CD48, CD53, CD69, CD70, CD72, CD73, CD79a, CD79b, CD80, CD81, CD83, CD85a, CD85d, CD85e, CD85h, CD85i, CD85j, CD85k, CD86, CD96, CD98, CD100, CD121b, CD124, CD127, CD132, CD150, CD152, CD154, CD157, CD166, CD169, CD179a, CD179b, CD180, CD185, CD196, CD197, CD205, CDw210a, CD213a1, CD257, CD267, CD268, CD269, CD274, CD275, CD276, CD278, CD279, CD300a, CD300c, CD307, CD314, CD316, CD317, CD319, CD320, CDw327, and CD331. In a particular embodiment, a cancer treated using the methods of the invention is associated with the expression of CD-20. In another embodiment, a cancer treated using the methods of the invention is associated with the expression of CD-22. In yet another embodiment, a cancer treated using the methods of the invention is associated with the expression of both CD-20 and CD-22.

In some embodiments, a cancer treated using the methods of the invention is non-Hodgkin's lymphoma or NHL. Non-Hodgkin's lymphoma or NHL, is a cancer of the lymphoid tissue which is formed by several types of immune cells including B-cells and T-cells. About 85% of the non-Hodgkin's lymphomas are derived from B-cells. NHL is thought to occur when B-cells, which produce antibodies, begin to grow abnormally. In some embodiments, non-Hodgkin's lymphoma treated using the methods of the invention is associated with the expression of CD-20 on B-cells. In other embodiments, non-Hodgkin's lymphoma is associated with the expression of CD-22. In yet other embodiments, non-Hodgkin's lymphoma is associated with the expression of both CD-20 and CD-22.

In some embodiments, a cancer treated using the methods of the invention is Hodgkin's lymphoma, also referred to as Hodgkin's disease. The cancer cells in Hodgkin's disease are called Reed-Sternberg cells, after the two doctors who first described them in detail. Under a microscope they look different from cells of non-Hodgkin's lymphomas and other cancers, and are believed to be a type of malignant B lymphocyte.

In some embodiments, a cancer treated using the methods of the invention is chronic lymphocytic leukemia (CLL) which is derived from a small B lymphocyte. CLL is mostly found in the blood and in the bone marrow.

In further embodiments, a cancer treated using the methods of the invention is mantle cell lymphoma.

In yet other embodiments, a cancer treated using the methods of the invention is multiple myeloma, associated with uncontrolled proliferation of antibody producing cells in the plasma, which develop from B-cells.

III. Exemplary Oxazaphosphorine Drugs

The methods of the present invention, are based, at least in part, on the discovery that high-dose pulsed amount of an oxazaphosphorine drug may be used for breaking immune tolerance, which presents a major obstacle in the use of immune therapeutics for the treatment of cancer such as, for example, monoclonal antibodies that bind cancer specific antigens.

Exemplary oxazaphosphorine drugs that may be used in the methods of the invention include, but are not limited to, for example, cyclophosphamide (CPA), ifosfamide (IFO), and trofosfamide. CPA is widely used in low to intermediate amounts as an anticancer drug, an immunosuppressant, and for the mobilization of hematopoetic progenitor cells from the bone marrow into peripheral blood prior to bone marrow transplantation for aplastic anemia, leukemia, and other malignancies. Additional oxazaphosphorine drugs that may be used in the methods of the invention include, for example, mafosfamide (NSC 345842), glufosfamide (D19575, beta-D-glucosylisophosphoramide mustard), NSC 612567 (aldophosphamide perhydrothiazine), and NSC 613060 (aldophosphamide thiazolidine).

Both CPA and IFO are prodrugs that require activation by hepatic cytochrome P450 (CYP)-catalyzed 4-hydroxylation, yielding cytotoxic nitrogen mustards capable of reacting with DNA molecules to form crosslinks and lead to cell apoptosis and/or necrosis. However, more newly synthesized oxazaphosphorine derivatives such as glufosfamide, NSC 612567 and NSC 613060, do not need hepatic activation. They are activated through other enzymatic and/or non-enzymatic pathways.

In some embodiments according to the present invention, an oxazaphosphorine drug is high-dose pulsed amount of cyclophosphamide.

IV. Exemplary Autologous Anti-Idiotypic Vaccines

In various embodiments of the methods of the present invention, an autologous anti-idiotypic vaccine is produced using a hybridoma technology. For example, a hybridoma cell-line may be developed which contains a tumor-specific antigen derived from a patient, which is unique to that patient and found exclusively on the surface of a B-lymphocyte associated with a B-cell derived cancer such as, for example, non-Hodgkin's lymphoma, Hodgkin's lymphoma, chronic lymphocytic leukemia, mantle cell lymphoma or multiple myeloma, and which is absent or expressed in decreased amounts in normal B-lymphocytes and other cells.

In some embodiments, an "autologous anti-idiotypic vaccine" includes an antigen associated with a B-cell derived cancer in a subject (e.g., non-Hodgkin's lymphoma, Hodgkin's lymphoma, chronic lymphocytic leukemia, mantle cell lymphoma or multiple myeloma) linked to KLH (keyhole limpet hemocyanin, a carrier protein). An exemplary autologous anti-idiotypic vaccine is BIOVAXID™.

V. Exemplary Antibodies

In various methods of the present invention, cancers derived from B-cells can be treated using a combination of a high-dose pulsed amount of an oxazaphosphorine drug and a monoclonal antibody which selectively binds a B-cell specific antigen in combination with an autologous anti-idiotypic vaccine.

In some embodiments of the present invention, an antibody is a monoclonal antibody that specifically binds CD-20 on a B-cell. In other embodiments, an antibody is a monoclonal antibody that specifically binds CD-22 on a B-cell. However, without wishing to be bound by theory, it is contemplated that a monoclonal antibody that selectively binds any one of B-cell specific antigens CD3d, CD5, CD6, CD9, CD19, CD20, CD21, CD22, CD23, CD24, CD27, CD28, CD37, CD38, CD40, CD45, CD46, CD48, CD53, CD69, CD70, CD72, CD73, CD79a, CD79b, CD80, CD81, CD83, CD85a, CD85d, CD85e, CD85h, CD85i, CD85j, CD85k, CD86, CD96, CD98, CD100, CD121b, CD124, CD127, CD132, CD150, CD152, CD154, CD157, CD166, CD169, CD179a, CD179b, CD180, CD185, CD196, CD197, CD205, CDw210a, CD213a1, CD257, CD267, CD268, CD269, CD274, CD275, CD276, CD278, CD279, CD300a, CD300c, CD307, CD314, CD316, CD317, CD319, CD320, CDw327, or CD331, may be used in the methods of the invention.

Commercially available monoclonal antibodies that specifically bind B-cell specific antigens include rituximab, which binds CD-20, and epratuzumab, which binds CD-22.

Antibodies or antigen-binding portions thereof can be tested for binding to a B-cell or a B-cell specific antigen by, for example, standard assays known in the art, such as ELISA, FACS analysis and/or Biacore analysis.

Antibodies or antigen-binding portions useful in the methods of the invention may be labeled with a detectable substance using well known techniques. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{14}C$, $^{123}I$, $^{124}I$, $^{125}I$, $^{131}I$, $^{99m}Tc$, $^{35}S$ or $^{3}H$.

IV. Modes of Administration

The various compounds used in the methods described herein may be administered orally, parenterally (e.g., intravenously), intramuscularly, sublingually, buccally, rectally, intranasally, intrabronchially, intrapulmonarily, intraperitonealy, topically, transdermally and subcutaneously, for example. The amount of compound administered in a single dose may dependent on the subject being treated, the subject's weight, the manner of administration and the judgment of the prescribing physician. Generally, however, administration and dosage and the duration of time for which a composition is administered will approximate that which are necessary to achieve a desired result.

For example, in some embodiments, a lymphocytotoxic non-myeloablative amount of an oxazaphosphorine drug used in the methods described herein is between 100 mg/kg and 200 mg/kg, administered daily from 1 to 7 days. In other embodiments, an effective amount of a lymphocytotoxic non-myeloablative amount of a oxazaphosphorine drug is between 25 mg/kg and 100 mg/kg, administered daily for 4 consecutive days. In yet other embodiments, a lymphocytotoxic non-myeloablative amount of a oxazaphosphorine drug is 50 mg/kg administered daily for 4 consecutive days.

In general, a therapeutically effective amount of a monoclonal antibody such as, for example, an antibody that specifically binds CD-20 or CD-22, from about 0.0001 mg/Kg to 0.001 mg/Kg; 0.001 mg/kg to about 10 mg/kg body weight or from about 0.02 mg/kg to about 5 mg/kg body weight. In some embodiments, a therapeutically effective amount of a monoclonal antibody is from about 0.001 mg to about 0.01 mg, about 0.01 mg to about 100 mg, or from about 100 mg to about 1000 mg, for example.

In some embodiments, an effective amount of an antibody administered to a subject having Hodgkin's lymphoma, Hodgkin's lymphoma, chronic lymphocytic leukemia or multiple myeloma between about 100 mg/m$^2$ and 200 mg/m$^2$, or between about 200 mg/m$^2$ and 300 mg/m$^2$ or between about 300 mg/m$^2$ and 400 mg/m$^2$. In a particular embodiment, an effective amount of a monoclonal antibody that selectively binds a B-cell specific antigen is about 375 mg/m$^2$.

The dose for the oxazaphosphorine drug, e.g., cyclophosphamide, for use in the methods of the present invention can be calculated according to the ideal body weight of the subject. Ideal body weight can be determined, for example, according to Metropolitan Life tables, or any other standard known in the art. If the patient's actual body weight is less than ideal, the actual weight may be used for the calculation of the oxazaphosphorine drug dose.

The optimal pharmaceutical formulations for a desired monoclonal antibody can be readily determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

Antibodies for use in the methods or compositions described herein can be formulated for the most effective route of administration, including for example, oral, transdermal, sublingual, buccal, parenteral, rectal, intranasal, intrabronchial or intrapulmonary administration.

In some embodiment, the vaccine compositions used in the methods of the present invention include one or more cytokines such as, for example, GM-CSF. GM-CSF is a potent immunostimulatory cytokine with efficacy in promoting antitumor response, particularly T cell responses. In general, however, any cytokine or chemokine that induces inflammatory responses, recruits antigen presenting cells (APC) to the tumor and, possibly, promotes targeting of antigen presenting cells (APC) may be used in the vaccine compositions.

The autologous anti-idiotypic vaccines useful in the methods of the present invention may be administered by any conventional route including oral and parenteral. Examples of parenteral routes are subcutaneous, intradermal, transcutaneous, intravenous, intramuscular, intraorbital, intracapsular, intrathecal, intraspinal, intracisternal, intraperitoneal, etc.

An effective amount of a vaccine composition administered to a subject will vary from individual to individual and can be, for example, between about 0.01 µg/kg and about 1 mg/kg body weight. The amount of the immunogen per dose can range from about 0.01 mg to 100 mg of protein per subject per injection.

Administration of the vaccine composition is preferably by injection on one or multiple occasions to produce systemic immunity. In general, multiple administrations of the vaccine in a standard immunization protocol are used, as is standard in the art. For example, the vaccines can be administered at approximately two to six week intervals, or monthly, for a period of from one to six inoculations in order to provide protection. The vaccine may be administered by any conventional route including oral and parenteral. Examples of parenteral routes are subcutaneous, intradermal, transcutaneous, intravenous, intramuscular, intraorbital, intracapsular, intrathecal, intraspinal, intracisternal, intraperitoneal, etc.

Without wishing to be bound by theory, it is contemplated that vaccination may result in a systemic immune response, which includes either or both of an antibody response and a cell-mediated immune response, which will provide an anticancer therapeutic effect and/or result in antibodies and activated T lymphocytes of various classes which may be used themselves as therapeutic agents, for example, for producing passive immunity in cancer-bearing subjects.

The vaccine compositions used in the methods of the present invention may further include one or more adjuvants or immunostimulatory agents. Examples of adjuvants and immunostimulatory agents include, but are not limited to, aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, whole organisms or subcellular fractions of the bacteria Propionobacterium acnes or Bordetella pertussis, polyribonucleotides, sodium alginate, lanolin, lysolecithin, vitamin A, saponin and saponin derivatives, liposomes, levamisole, DEAE-dextran, blocked copolymers or other synthetic adjuvants. Such adjuvants are readily commercially available.

In some embodiments, the present invention provides kits including one or more doses of high-dose pulsed amount of an oxazaphosphorine drug and/or one or more doses of an immune therapeutic such as, for example, a B-cell specific monoclonal antibody, packaged with instructions of use. Such instructions may pertain to use of the packaged components (i.e., one or more doses of a high-dose pulsed amount of an oxazaphosphorine drug and/or one or more doses of a B-cell specific monoclonal antibody and/or one or more doses of an autologous anti-idiotypic vaccine) in methods of treating, preventing, ameliorating, eliminating or substantially reducing Hodgkin's lymphoma, non-Hodgkin's lymphoma, chronic lymphocytic leukemia, mantle cell lymphoma or multiple myeloma, in a patient, or a symptom associated with Hodgkin's lymphoma, non-Hodgkin's lymphoma, chronic lymphocytic leukemia, mantle cell lymphoma or multiple myeloma in a patient, by administering the one or more doses of high-dose pulsed amount of an oxazaphosphorine drug and/or one or more doses of a B-cell specific monoclonal antibody and/or one or more doses of an autologous anti-idiotypic vaccine.

Depending on the intended mode of administration, the compounds used in the methods described herein may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. Each dose may include an effective amount of a compound used in the methods described herein in combination with a pharmaceutically acceptable carrier and, in addition, may include other medicinal agents, pharmaceutical agents, carriers, adjuvants, diluents, etc.

Liquid pharmaceutically administrable compositions can prepared, for example, by dissolving, dispersing, etc., a compound for use in the methods described herein and optional pharmaceutical adjuvants in an excipient, such as, for example, water, saline aqueous dextrose, glycerol, ethanol, and the like, to thereby form a solution or suspension. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; see, for example, Remington's Pharmaceutical Sciences, 18th Ed. (1990), Mack Publishing Co., Easton, Pa., the entire disclosure of which is hereby incorporated by reference).

V. Methods of Treatment

Methods of treatment described herein encompass methods of eliminating or substantially reducing a B-cell derived cancer such as, for example, non-Hodgkin's lymphoma, Hodgkin's lymphoma, chronic lymphocytic leukemia, mantle cell lymphoma and multiple myeloma. Also encompassed are methods of eliminating immune cells which are capable of eliciting immune tolerance. All methods described herein exclude the use of stem cell transplantation.

A subject having non-Hodgkin's lymphoma, Hodgkin's lymphoma, chronic lymphocytic leukemia, mantle cell lymphoma or multiple myeloma can be diagnosed using standard techniques known in the art. For example, a diagnosis may be made by removing a part of a lymph node and examining the cells under a microscope. Biopsies may also be taken from other body tissues.

Subsequent to diagnosis, a subject having non-Hodgkin's lymphoma, Hodgkin's lymphoma, chronic lymphocytic leukemia, mantle cell lymphoma or multiple myeloma can be treated using methods of the invention.

In some embodiments, a subject having non-Hodgkin's lymphoma or Hodgkin's lymphoma or chronic lymphocytic leukemia, mantle cell lymphoma or multiple myeloma is administered a lymphocytotoxic but hematopoeitic stem cell sparing high-dose pulsed amount of an oxazaphosphorine drug, e.g., 50 mg/kg of cyclophosphamide administered daily for 4 days, followed by an effective amount of an autologous-idiotypic vaccine, which may optionally be administered in conjunction with an effective amount of GM-CSF.

In some embodiments, a subject having non-Hodgkin's lymphoma or Hodgkin's lymphoma or chronic lymphocytic leukemia or mantle cell lymphoma or multiple myeloma is administered a lymphocytotoxic but hematopoeitic stem cell sparing high-dose pulsed amount of an oxazaphosphorine drug, e.g., 50 mg/kg of cyclophosphamide administered daily for 4 days, followed by an effective amount of an autologous-idiotypic vaccine (optionally in conjunction with GM-CSF) and an effective amount of a monoclonal antibody which specifically binds a B-cell specific antigen, e.g., CD-20 or CD-22.

The specification is most thoroughly understood in light of the teachings of the references cited within the specification which are hereby incorporated by reference. The embodiments within the specification provide an illustration of embodiments in this disclosure and should not be construed to limit its scope. The skilled artisan readily recognizes that many other embodiments are encompassed by this invention. All publications and patents cited and sequences identified by accession or database reference numbers in this disclosure are incorporated by reference in their entirety. To the extent that the material incorporated by reference contradicts or is inconsistent with the present specification, the present specification will supercede any such material. The citation of any references herein is not an admission that such references are prior art to the present disclosure.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention claimed is:

1. A method for eliminating or substantially reducing a B-cell derived cancer in a subject comprising administering a lymphocytotoxic but hematopoietic stem cell sparing high-dose pulsed amount of an oxazaphosphorine drug to the subject, such that the subject's immune system reconstitutes without stem cell transplantation, administering to the subject one or more monoclonal antibodies that selectively bind to a B-cell specific antigen, and administering an effective amount of an autologous anti-idiotypic vaccine, thereby to eliminate or substantially reduce the B-cell derived cancer in the subject.

2. The method of claim 1, wherein the B-cell derived cancer is selected from the group consisting of non-Hodgkin's lymphoma, Hodgkin's lymphoma, mantle cell lymphoma, chronic lymphocytic leukemia and multiple myeloma.

3. The method of claim 1, wherein the autologous anti-idiotypic vaccine is administered in conjunction with an effective amount of granulocyte-monocyte colony stimulating factor.

4. The method of claim 1, wherein the B-cell specific antigen is selected from the group consisting of CD3d, CD5, CD6, CD9, CD19, CD20, CD21, CD22, CD23, CD24, CD27, CD28, CD37, CD38, CD40, CD45, CD46, CD48, CD53, CD69, CD70, CD72, CD73, CD79a, CD79b, CD80, CD81, CD83, CD85a, CD85d, CD85e, CD85h, CD85i, CD85j, CD85k, CD86, CD96, CD98, CD100, CD121b, CD124, CD127, CD132, CD150, CD152, CD154, CD157, CD166, CD169, CD179a, CD179b, CD180, CD185, CD196, CD197, CD205, CDw210a, CD213a1, CD257, CD267, CD268, CD269, CD274, CD275, CD276, CD278, CD279, CD300a, CD300c, CD307, CD314, CD316, CD317, CD319, CD320, CDw327, and CD331.

5. The method of claim 1, wherein the one or more monoclonal antibodies selectively binds to CD-20.

6. The method of claim 1, wherein the one or more monoclonal antibodies selectively binds to CD-22.

7. The method of claim 1, wherein the amount of an oxazaphosphorine drug is 50 mg/kg/day.

8. The method of claim 1, wherein the oxazaphosphorine drug is administered to the subject for 4 days.

9. The method of claim 1, wherein the oxazaphosphorine drug administered to the subject at a dose of 50 mg/kg/day for 4 days.

10. The method of claim 1, wherein the oxazaphosphorine drug is cyclophosphamide administered in the amount of 50 mg/Kg for 4 days.

11. The method of claim 1, wherein the oxazaphosphorine drug is powdered cyclophosphamide or a pharmaceutically acceptable salt, solvate, prodrug, or metabolite thereof.

12. The method of claim 1, wherein the oxazaphosphorine drug is lyophilized cyclophosphamide or a pharmaceutically acceptable salt, solvate, prodrug, or metabolite thereof.

13. The method of claim 1, further comprising administering an effective amount of Mesna.

14. The method of claim 1, wherein the autologous anti-idiotypic vaccine and the one or more monoclonal antibodies are administered after administration of the oxazaphosphorine drug.

15. A method of eliminating or substantially reducing a B-cell derived cancer selected from the group consisting of non-Hodgkin's lymphoma, Hodgkin's lymphoma, mantle cell lymphoma, chronic lymphocytic leukemia and multiple myeloma in a subject comprising administering to the subject: (a) a lymphocytotoxic but hematopoietic stem cell sparing high-dose pulsed amount of an oxazaphosphorine drug; (b) an effective amount of an autologous anti-idiotypic vaccine in conjunction with an effective amount of GM-CSF; and (c) an effective amount of one or more monoclonal antibodies that selectively bind one or more B-cell specific antigens, thereby eliminating or substantially reducing the B-cell derived cancer in the subject.

16. The method of claim 15, wherein the autologous anti-idiotypic vaccine and the one or more monoclonal antibodies are administered after administration of the oxazaphosphorine drug.

17. The method of claim 15, wherein the B-cell specific antigen is selected from the group consisting of CD3d, CD5, CD6, CD9, CD19, CD20, CD21, CD22, CD23, CD24, CD27, CD28, CD37, CD38, CD40, CD45, CD46, CD48, CD53, CD69, CD70, CD72, CD73, CD79a, CD79b, CD80, CD81, CD83, CD85a, CD85d, CD85e, CD85h, CD85i, CD85j, CD85k, CD86, CD96, CD98, CD100, CD121b, CD124, CD127, CD132, CD150, CD152, CD154, CD157, CD166, CD169, CD179a, CD179b, CD180, CD185, CD196, CD197, CD205, CDw210a, CD213a1, CD257, CD267, CD268, CD269, CD274, CD275, CD276, CD278, CD279, CD300a, CD300c, CD307, CD314, CD316, CD317, CD319, CD320, CDw327, and CD331.

18. The method of claim 15, wherein the one or more monoclonal antibodies selectively binds to CD-20.

19. The method of claim 15, wherein the one or more monoclonal antibodies selectively binds to CD-22.

20. The method of claim 15, wherein the amount of an oxazaphosphorine drug is 50 mg/kg/day.

21. The method of claim 15, wherein the oxazaphosphorine drug is administered to the subject for 4 days.

22. The method of claim 15, wherein the oxazaphosphorine drug administered to the subject at a dose of 50 mg/kg/day for 4 days.

23. The method of claim 15, wherein the oxazaphosphorine drug is cyclophosphamide administered in the amount of 50 mg/Kg for 4 days.

24. The method of claim 15, wherein the oxazaphosphorine drug is powdered cyclophosphamide or a pharmaceutically acceptable salt, solvate, prodrug, or metabolite thereof.

25. The method of claim 15, wherein the oxazaphosphorine drug is lyophilized cyclophosphamide or a pharmaceutically acceptable salt, solvate, prodrug, or metabolite thereof.

26. The method of claim 15, further comprising administering an effective amount of Mesna.

* * * * *